United States Patent
Knight et al.

(10) Patent No.: US 12,249,064 B2
(45) Date of Patent: Mar. 11, 2025

(54) DIGITAL IMAGING SYSTEMS AND METHODS OF ANALYZING PIXEL DATA OF AN IMAGE OF A SKIN AREA OF A USER FOR DETERMINING SKIN PUFFINESS

(71) Applicant: The Gillette Company LLC, Boston, MA (US)

(72) Inventors: Leigh Knight, Reading (GB); Robyn Dolbear, Reading (GB); Rachel Russell, Reading (GB); Kate Budds, Reading (GB); Katie Wilson, Reading (GB)

(73) Assignee: The Gillette Company LLC, Cincinnati, OH (US)

( * ) Notice: Subject to any disclaimer, the term of this patent is extended or adjusted under 35 U.S.C. 154(b) by 600 days.

(21) Appl. No.: 17/553,596

(22) Filed: Dec. 16, 2021

(65) Prior Publication Data
US 2023/0196549 A1 Jun. 22, 2023

(51) Int. Cl.
*G06T 7/00* (2017.01)
(52) U.S. Cl.
CPC .. *G06T 7/0012* (2013.01); *G06T 2207/20081* (2013.01); *G06T 2207/20084* (2013.01); *G06T 2207/30088* (2013.01)
(58) Field of Classification Search
CPC ......... G06T 7/0012; G06T 2207/20081; G06T 2207/20084; G06T 2207/30088
See application file for complete search history.

(56) References Cited

U.S. PATENT DOCUMENTS 10,818,007 B2  10/2020  Purwar et al.
11,901,080 B1   2/2024  Matt
(Continued)

FOREIGN PATENT DOCUMENTS

CN  110298815 A  10/2019
CN  111428552 A   7/2020
(Continued)

OTHER PUBLICATIONS

All Office Actions; U.S. Appl. No. 17/553,611, filed on Dec. 16, 2021.
(Continued)

*Primary Examiner* — Kevin Ky
(74) *Attorney, Agent, or Firm* — Andres E. Velarde; Kevin C. Johnson

(57) ABSTRACT

Digital imaging systems and methods are described for analyzing pixel data of an image of a skin area of a user for determining skin puffiness. A plurality of training images of a plurality of individuals are aggregated, each of the training images comprising pixel data of a respective skin area of an individual. A skin puffiness model, trained with the pixel data, is operable to output, across a range of a skin puffiness scale, skin puffiness values associated with a degree of skin puffiness. An image of a user comprising pixel data of at least a portion of a user skin area is received and analyzed, by the skin puffiness model, to determine a user-specific skin puffiness value of the user skin area. A user-specific electronic recommendation addressing at least one feature identifiable within the pixel data is generated and rendered, on a display screen of a user computing device.

16 Claims, 4 Drawing Sheets

(56) References Cited

U.S. PATENT DOCUMENTS

| | | | |
|---|---|---|---|
| 11,908,128 | B2 | 2/2024 | Jiang |
| 11,998,334 | B2* | 6/2024 | Berthier ............ A61B 5/150099 |
| 2003/0065578 | A1 | 4/2003 | Peyrelevade et al. |
| 2004/0264750 | A1 | 12/2004 | Znaiden et al. |
| 2008/0194928 | A1 | 8/2008 | Bandic |
| 2010/0185064 | A1 | 7/2010 | Bandic et al. |
| 2012/0314920 | A1 | 12/2012 | Prigent |
| 2014/0323873 | A1 | 10/2014 | Cummins |
| 2017/0270593 | A1 | 9/2017 | Sherman et al. |
| 2018/0033205 | A1 | 2/2018 | Kong et al. |
| 2018/0350071 | A1 | 12/2018 | Purwar |
| 2019/0213453 | A1 | 7/2019 | Ludwinski et al. |
| 2019/0237194 | A1 | 8/2019 | Salvi et al. |
| 2020/0042769 | A1* | 2/2020 | Yan ....................... G06F 18/217 |
| 2020/0170564 | A1 | 6/2020 | Jiang et al. |
| 2020/0250404 | A1 | 8/2020 | Shinoda |
| 2020/0342594 | A1 | 10/2020 | Dissanayake |
| 2021/0012493 | A1 | 1/2021 | Jiang et al. |
| 2021/0142111 | A1 | 5/2021 | Yao |
| 2021/0142890 | A1 | 5/2021 | Adiri et al. |
| 2021/0174965 | A1 | 6/2021 | Thubagere Jagadeesh et al. |
| 2021/0182705 | A1 | 6/2021 | Bates |
| 2021/0286975 | A1 | 9/2021 | Sun |
| 2022/0019765 | A1 | 1/2022 | Yao |
| 2022/0051409 | A1 | 2/2022 | Maclellan |
| 2022/0224876 | A1 | 7/2022 | Matts et al. |
| 2022/0237751 | A1 | 7/2022 | Bradley |
| 2022/0237811 | A1 | 7/2022 | Cai et al. |
| 2022/0309668 | A1 | 9/2022 | Swart |
| 2022/0344044 | A1 | 10/2022 | Yoo |
| 2022/0359062 | A1 | 11/2022 | Dunn |
| 2023/0029766 | A1 | 2/2023 | Jay |
| 2023/0074782 | A1* | 3/2023 | Tendulkar .............. G06V 10/56 |
| 2023/0077452 | A1* | 3/2023 | Cardelino ............. G16H 20/10 600/306 |
| 2023/0116487 | A1* | 4/2023 | Tendulkar ............ G06T 7/0012 382/128 |
| 2023/0255544 | A1 | 8/2023 | Goyal |
| 2024/0148999 | A1* | 5/2024 | Hartono .............. A61M 16/109 |

FOREIGN PATENT DOCUMENTS

| | | |
|---|---|---|
| CN | 111985458 A | 11/2020 |
| CN | 112084965 A | 12/2020 |
| CN | 112541394 A | 3/2021 |
| CN | 113298841 A | 8/2021 |
| CN | 113610844 A | 11/2021 |
| EP | 3816932 A1 | 5/2021 |
| EP | 3933774 A1 | 1/2022 |
| EP | 3933851 A1 | 1/2022 |
| KR | 102135874 B1 | 7/2020 |
| WO | 0233628 A2 | 4/2002 |

OTHER PUBLICATIONS

All Office Actions; U.S. Appl. No. 17/553,619, filed on Dec. 16, 2021.

All Office Actions; U.S. Appl. No. 17/553,632, filed on Dec. 16, 2021.

All Office Actions; U.S. Appl. No. 17/553,655, filed on Dec. 16, 2021.

All Office Actions; U.S. Appl. No. 17/553,666, filed on Dec. 16, 2021.

All Office Actions; U.S. Appl. No. 17/553,659, filed on Dec. 16, 2021.

All Office Actions; U.S. Appl. No. 17/553,647, filed on Dec. 16, 2021.

U.S. Appl. No. 17/553,611, filed Dec. 16, 2021, to Leigh Knight et al.

U.S. Appl. No. 17/553,619, filed Dec. 16, 2021, to Leigh Knight et al.

U.S. Appl. No. 17/553,632, filed Dec. 16, 2021, to Leigh Knight et al.

U.S. Appl. No. 17/553,647, filed Dec. 16, 2021, to Leigh Knightr et al.

U.S. Appl. No. 17/553,655, filed Dec. 16, 2021, to Leigh Knight et al.

U.S. Appl. No. 17/553,659, filed Dec. 16, 2021, to Leigh Knightr et al.

U.S. Appl. No. 17/553,666, filed Dec. 16, 2021, to Leigh Knight et al.

Hsia Chih-Hsien et al: "System for Recommending Facial Skincare Products", Sensors and Materials, vol. 32, No. 10, Oct. 9, 2020, pp. 3235-3242.

Kohli Indermeet et al: "Quantitative measurement of skin surface oiliness and shine using differential polarized images", Archives of Dermatological Research, vol. 313, No. 2, Apr. 8, 2020, pp. 71-77.

Kothari Arya et al: "Cosmetic Skin Type Classification Using CNN With Product Recommendation", 2021 12th International Conference on Computing Communication and Networking Technologies (ICCCNT), Jul. 6-8, 2021, 6 pages.

Li Hsiao-Hui et al: "Based on machine learning for personalized skin care products recommendation engine", 2020 International Symposium on Computer, Consumer and Control (IS3C), Nov. 13, 2020, 3 pages.

Mueller Willem: " DeepSkin: Mobile-Based Skin Quality Assessment with Deep Learning", Aug. 31, 2020, 180 pages.

Nissa Farhan Novia et al: "Application of Deep Learning Using Convolutional Neural Network (CNN) Method for Women's Skin Classification", Scientific Journal of Informatics, vol. 8, No. 1, May 2021, pp. 144-153.

Pierrard Jean-Sebastien et al: "Skin Detail Analysis for Face Recognition", 2007 IEEE Conference on Computer Vision and Pattern Recognition, Jun. 1, 2007, 8 pages.

Tianxing Li et al: "Lightweight Real-time Makeup Try-on in Mobile Browsers with Tiny CNN Models for Facial Tracking", Arxiv.Org, Cornell University Library, Jun. 5, 2019, 4 pages.

PCT Search Report and Written Opinion for PCT/US2022/081369 dated Apr. 19, 2023, 17 pages.

Min Chen et al. "AI-Skin: Skin disease recognition based on self-learning and wide data collection through a closed-loop framework", Information Fusion 54, Jun. 2, 2019, pp. 1-9.

A. Kothari, "Cosmetic Skin Type Classification Using CNN With Product Recommendation", 2021 12th International Conference on Computing Communication and Networking Technologies (1000NT), Kharagpur, India, 2021, pp. 1-6, doi: 10.1109/ 1000NT51525.202i. 9580174. keywords: {D (Year: 2021).

P. R. H. Perera, "Virtual Makeover and Makeup Recommendation Based on Personal Trait Analysis", 2021 3rd 2 International Conference on Advancements in Computing (ICAC), Colombo, Sri Lanka, 2021, pp. 288-293, (Year: 2021).

Cula, et al., Skin Texture Modeling, International Journal of Computer Vision, vol. 62, Issue 1/2, Nov. 2004, pp. 97-119.

* cited by examiner

DIGITAL IMAGING SYSTEMS AND METHODS OF ANALYZING PIXEL DATA OF AN IMAGE OF A SKIN AREA OF A USER FOR DETERMINING SKIN PUFFINESS

FIELD OF THE INVENTION

The present disclosure generally relates to digital imaging systems and methods, and more particularly to digital imaging systems and methods of analyzing pixel data of an image of a skin area of a user for determining skin puffiness.

BACKGROUND OF THE INVENTION

Individuals can develop puffy skin in various spots on their bodies. Skin puffiness describes the quality or state of skin being swollen or taught. The skin is the body's largest organ, and like the other organs, its health, and as a result its appearance, is affected by various factors including age, exposure to toxins, harsh weather, nutrient deficiencies, and individual habits, such as smoking. Skin puffiness can be most noticeable to others when it's on an individual's face. But other parts of the head r body can also show signs of skin puffiness as well.

In some instances, highly reactive chemical compounds, generally referred to as free radicals, can also contribute to skin puffiness. Chronic exposure to free radicals can cause damage to human cells, tissues, and organs of the body, including the skin. Over time, exposure to free radicals can cause an individual's skin to be less healthy and begin to loosen and droop. This happens in part because of damage to the proteins that hold the skin firmly to the muscles, tendons, fatty tissue, and/or other structural components that surround it.

In addition, puffy skin on the face is also common in those who gain weight. Similarly, repetitive facial movements, chronic unmanaged stress, the effects of gravity, and even the position that a person sleeps in, can each also contribute to skin puffiness.

A main cause of skin puffiness is aging because, with age, levels of two very important connective proteins diminish. These are collagen, which is the most abundant protein in all animals, and elastin, which helps the skin snap back into its original position after being stretched. Young skin tissue has plentiful amounts of both collagen and elastin. However, with age and exposure to sunshine, levels of both tend to drop off significantly.

An effective way of boosting elastin and collagen levels is to activate fibroblast cells, which produce elastin and collagen. Generally, fibroblast cells are present in the dermis, which is the second layer of the skin that is found under the outer layer (epidermis). Stimulating these cells increases the production of collagen and elastin, which can enhance the strength, firmness, resilience, and appearance of the skin.

Use of cosmeceutical products, skin creams, and/or other such skin puffiness products can be used to active fibroblasts for the boosting of collagen and elastin production or otherwise mitigation of the appearance of skin puffiness. However, such products are typically differently formulated and/or designed to address different ages, skin types, and/or body areas of a multitude of individuals, where a given cosmeceutical product, skin cream, and/or other such skin puffiness products product may affect one individual having a first set of age and/or otherwise skin puffiness characteristics differently than a second individual having a second set of age and/or otherwise skin puffiness characteristics. The problem is acutely pronounced given the various versions, brands, and types of cosmeceutical products, skin creams, and/or other such skin puffiness products currently available to individuals, where each of these different versions, brands, and types of products have different chemical compositions, ingredients, and/or otherwise different designs or formulations, all of which can vary significantly in their capability and effectiveness of treating skin puffiness of a specific individual. This problem is particularly acute because such existing skin puffiness products—which may be differently designed or formulated—provide little or no feedback or guidance to assist an individual address his or her own personal skin puffiness issues.

For the foregoing reasons, there is a need for digital imaging systems and methods of analyzing pixel data of an image of a skin area of a user for determining skin puffiness.

SUMMARY OF THE INVENTION

Generally, as described herein, the digital imaging systems and methods of analyzing pixel data of an image of a skin area of a user for determining skin puffiness, provide a digital imaging, and artificial intelligence (AI), based solution for overcoming problems, whether actual or perceived, that arise from skin puffiness issues. As described herein, skin puffiness refers to the quality or state of skin being swollen or tight.

The digital systems and methods described herein allow a user to submit a specific user image to imaging server(s) (e.g., including its one or more processors), or otherwise a computing device (e.g., such as locally on the user's mobile device), where the imaging server(s) or user computing device implements or executes a skin puffiness model trained with pixel data of potentially 10,000 s (or more) images of individuals having various degrees of skin puffiness. The skin puffiness model may generate, based on a skin puffiness value of a user's skin area, a user-specific electronic recommendation designed to address at least one feature identifiable within the pixel data comprising the at least the portion of the user skin area. For example, the at least one feature can comprise pixels or pixel data indicative of a degree of skin puffiness, from least puffiness to most puffiness (based on puffiness values across a range of puffiness values determined in training images of individuals' respective skin areas). In some embodiments, the user-specific recommendation (and/or product specific recommendation) may be transmitted via a computer network to a user computing device of the user for rendering on a display screen. In other embodiments, no transmission to the imaging server of the user's specific image occurs, where the user-specific recommendation (and/or product specific recommendation) may instead be generated by the skin puffiness model, executing and/or implemented locally on the user's mobile device and rendered, by a processor of the mobile device, on a display screen of the mobile device. In various embodiments, such rendering may include graphical representations, overlays, annotations, and the like for addressing the feature in the pixel data.

More specifically, as describe herein, a digital imaging method of analyzing pixel data of an image of a skin area of a user for determining skin puffiness is disclosed. The digital imaging method comprises: (a) aggregating, at one or more processors communicatively coupled to one or more memories, a plurality of training images of a plurality of individuals, each of the training images comprising pixel data of a skin area of a respective individual; (b) training, by the one or more processors with the pixel data of the plurality of training images, a skin puffiness model comprising a skin puffiness scale and operable to output, across a range of the skin puffiness scale, skin puffiness values associated with a degree of skin puffiness ranging from least puffiness to most puffiness; (c) receiving, at the one or more processors, at least one image of a user, the at least one image captured by a digital camera, and the at least one image comprising pixel data of at least a portion of a user skin area of the user; (d) analyzing, by the skin puffiness model executing on the one or more processors, the at least one image captured by the digital camera to determine a user-specific skin puffiness value of the user skin area; (e) generating, by the one or more processors based on the user-specific skin puffiness value, at least one user-specific electronic recommendation designed to address at least one feature identifiable within the pixel data comprising the at least the portion of the user skin area; and (f) rendering, on a display screen of a user computing device, the at least one user-specific recommendation.

In addition, as described herein, a digital imaging system is disclosed, configured to analyze pixel data of an image of a skin area of a user for determining skin puffiness, the digital imaging system comprising: an imaging server comprising a server processor and a server memory; an imaging application (app) configured to execute on a user computing device comprising a device processor and a device memory, the imaging app communicatively coupled to the imaging server; and a skin puffiness model trained with pixel data of a plurality of training images of individuals and operable to output, across a range of a skin puffiness scale, skin puffiness values associated with a degree of skin puffiness ranging from least puffiness to most puffiness, wherein the skin puffiness model is configured to execute on the server processor or the device processor to cause the server processor or the device processor to: receive, at the one or more processors, at least one image of a user, the at least one image captured by a digital camera, and the at least one image comprising pixel data of at least a portion of a user skin area of the user; analyze, by the skin puffiness model executing on the one or more processors, the at least one image captured by the digital camera to determine a user-specific skin puffiness value of the user skin area; generate, by the one or more processors based on the user-specific skin puffiness value, at least one user-specific electronic recommendation designed to address at least one feature identifiable within the pixel data comprising the at least the portion of the user skin area; and render, on a display screen of a user computing device, the at least one user-specific recommendation.

Further, as described herein, a tangible, non-transitory computer-readable medium storing instructions for analyzing pixel data of an image of a skin area of a user for determining skin puffiness is disclosed. The instructions, when executed by one or more processors may cause the one or more processors to: (a) aggregate, at one or more processors communicatively coupled to one or more memories, a plurality of training images of a plurality of individuals, each of the training images comprising pixel data of a skin area of a respective individual; (b) train, by the one or more processors with the pixel data of the plurality of training images, a skin puffiness model comprising a skin puffiness scale and operable to output, across a range of the skin puffiness scale, skin puffiness values associated with a degree of skin puffiness ranging from least puffiness to most puffiness; (c) receive, at the one or more processors, at least one image of a user, the at least one image captured by a digital camera, and the at least one image comprising pixel data of at least a portion of a user skin area of the user; (d) analyze, by the skin puffiness model executing on the one or more processors, the at least one image captured by the digital camera to determine a user-specific skin puffiness value of the user skin area; (e) generate, by the one or more processors based on the user-specific skin puffiness value, at least one user-specific electronic recommendation designed to address at least one feature identifiable within the pixel data comprising the at least the portion of the user skin area; and (f) render, on a display screen of a user computing device, the at least one user-specific recommendation.

In accordance with the above, and with the disclosure herein, the present disclosure includes improvements in computer functionality or in improvements to other technologies at least because the disclosure describes that, e.g., an imaging server, or otherwise computing device (e.g., a user computer device), is improved where the intelligence or predictive ability of the imaging server or computing device is enhanced by a trained (e.g., machine learning trained) skin puffiness model. The skin puffiness model, executing on the imaging server or computing device, is able to accurately identify, based on pixel data of other individuals, a user-specific skin puffiness value for at least a portion of a user skin area and a user-specific electronic recommendation designed to address at least one feature identifiable within the pixel data of a specific user comprising the at least the portion of the user skin area. That is, the present disclosure describes improvements in the functioning of the computer itself or "any other technology or technical field" because an imaging server or user computing device is enhanced with a plurality of training images (e.g., 10,000 s of training images and related pixel data as feature data) to accurately predict, detect, or determine pixel data of a user-specific images, such as newly provided customer images. This improves over the prior art at least because existing systems lack such predictive or classification functionality and are simply not capable of accurately analyzing user-specific images to output a predictive result to address at least one feature (e.g., related to skin puffiness) identifiable within the pixel data comprising the at least the portion of the user skin area.

For similar reasons, the present disclosure relates to improvement to other technologies or technical fields at least because the present disclosure describes or introduces improvements to computing devices in the field(s) of skin puffiness and/or dermatology, whereby the trained skin puffiness model executing on the imaging device(s) or computing devices improve the field(s) of skin puffiness and/or dermatology with digital and/or artificial intelligence based analysis of user or individual images to output a predictive result to address user-specific pixel data of at least one feature identifiable within the pixel data comprising the at least the least the portion of the user skin area.

In addition, the present disclosure includes specific features other than what is well-understood, routine, conventional activity in the field, or adding unconventional steps that confine the claim to a particular useful application, e.g., analyzing pixel data of an image of a skin area of a user for determining skin puffiness as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

The Figures depict preferred embodiments for purposes of illustration only. Alternative embodiments of the systems and methods illustrated herein may be employed without departing from the principles of the invention described herein.

DETAILED DESCRIPTION OF THE INVENTION

Figure 1:
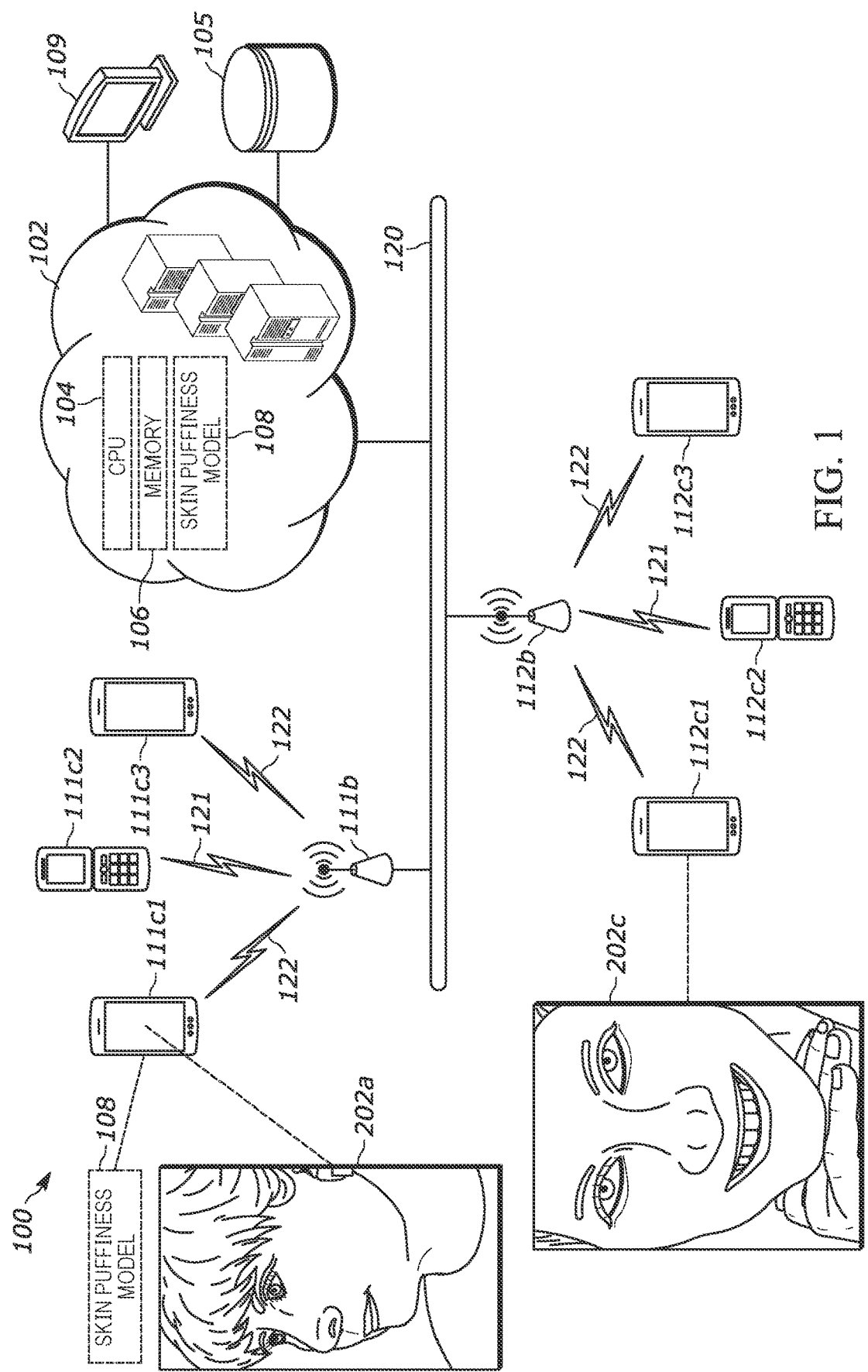
FIG. 1 illustrates an example digital imaging system configured to analyze pixel data of an image of a skin area of a user for determining skin puffiness, in accordance with various embodiments disclosed herein.

FIG. 1 illustrates an example digital imaging system 100 configured to analyze pixel data of an image (e.g., any one or more of images 202a, and/or 202c) of a skin area, or otherwise body or body area, of a user for determining skin puffiness, in accordance with various embodiments disclosed herein. As referred to herein, a "body" may refer to any portion of the human body including the face, head, and neck. In the example embodiment of FIG. 1, digital imaging system 100 includes server(s) 102, which may comprise one or more computer servers. In various embodiments server(s) 102 comprise multiple servers, which may comprise a multiple, redundant, or replicated servers as part of a server farm. In still further embodiments, server(s) 102 may be implemented as cloud-based servers, such as a cloud-based computing platform. For example, imaging server(s) 102 may be any one or more cloud-based platform(s) such as MICROSOFT AZURE, AMAZON AWS, or the like. Server(s) 102 may include one or more processor(s) 104 as well as one or more computer memories 106. Server(s) 102 may be referred to herein as "imaging server(s)."

The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memorie(s) 106 may store an operating system (OS) (e.g., Microsoft Windows, Linux, UNIX, etc.) capable of facilitating the functionalities, apps, methods, or other software as discussed herein. The memorie(s) 106 may also store a skin puffiness model 108, which may be an artificial intelligence based model, such as a machine learning model, trained on various images (e.g., images 202a, and/or 202c), as described herein. Additionally, or alternatively, the skin puffiness model 108 may also be stored in database 105, which is accessible or otherwise communicatively coupled to imaging server(s) 102. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the skin puffiness model 108, where each may be configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 104 (e.g., a relational database, such as Oracle, DB2, MySQL, or a NoSQL based database, such as MongoDB). The data stored in the memories 106 and/or the database 105 may include all or part of any of the data or information described herein, including, for example, training images and/or user images (e.g., either of which including any one or more of images 202a, and/or 202c) or other information of the user, including demographic, age, race, skin type, or the like.

The imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some embodiments, imaging server(s) 102 may include a client-server platform technology such as ASP.NET, Java J2EE, Ruby on Rails, Node.js, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some embodiments, computer network 120 may comprise a private network or local area network (LAN). Additionally, or alternatively, computer network 120 may comprise a public network such as the Internet.

Imaging server(s) 102 may further include or implement an operator interface configured to present information to an administrator or operator and/or receive inputs from the administrator or operator. As shown in FIG. 1, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via or attached to imaging server(s) 102 or may be indirectly accessible via or attached to terminal 109. According to some embodiments, an administrator or operator may access the server 102 via terminal 109 to review information, make changes, input training data or images, and/or perform other functions.

As described above herein, in some embodiments, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, imaging server(s) 102 are communicatively connected, via computer network 120 to the one or more user computing devices 111c1-111c3 and/or 112c1-112c3 via base stations 111b and 112b. In some embodiments, base stations 111b and 112b may comprise cellular base stations, such as cell towers, communicating to the one or more user computing devices 111c1-111c3 and 112c1-112c3 via wireless communications 121 based on any one or more of various mobile phone standards, including NMT, GSM, CDMA, UMMTS, LTE, 5G, or the like. Additionally or alternatively, base stations 111b and 112b may comprise routers, wireless switches, or other such wireless connection points communicating to the one or more user computing devices 111c1-111c3 and 112c1-112c3 via wireless communications 122 based on any one or more of various wireless standards, including by non-limiting example, IEEE 802.11a/b/c/g (WIFI), the BLUETOOTH standard, or the like.

Any of the one or more user computing devices 111c1-111c3 and/or 112c1-112c3 may comprise mobile devices and/or client devices for accessing and/or communications with imaging server(s) 102. In various embodiments, user computing devices 111c1-111c3 and/or 112c1-112c3 may comprise a cellular phone, a mobile phone, a tablet device, a personal data assistance (PDA), or the like, including, by non-limiting example, an APPLE iPhone or iPad device or a GOOGLE ANDROID based mobile phone or table. In still further embodiments, user computing devices 111c1-111c3 and/or 112c1-112c3 may comprise a home assistant device and/or personal assistant device, e.g., having display screens, including, by way of non-limiting example, any one or more of a GOOGLE HOME device, an AMAZON ALEXA device, an ECHO SHOW device, or the like. In additional embodiments, user computing devices 111c1-111c3 and/or 112c1-112c3 may comprise a retail computing device. A retail computing device would be configured in the same or similar manner, e.g., as described herein for user computing devices 111c1-111c3, including having a processor and memory, for implementing, or communicating with (e.g., via server(s) 102), a skin puffiness model 108 as described herein. However, a retail computing device may be located, installed, or otherwise positioned within a retail environment to allow users and/or customers of the retail environment to utilize the digital imaging systems and methods on site within the retail environment. For example, the retail computing device may be installed within a kiosk for access by a user. The user may then upload or transfer images (e.g., from a user mobile device) to the kiosk to implement the digital imaging systems and methods described herein. Additionally, or alternatively, the kiosk may be configured with a camera to allow the user to take new images (e.g., in a private manner where warranted) of himself or herself for upload and transfer. In such embodiments, the user or consumer himself or herself would be able to use the retail computing device to receive and/or have rendered a user-specific electronic recommendation, as described herein, on a display screen of the retail computing device. Additionally, or alternatively, the retail computing device may be a mobile device (as described herein) as carried by an employee or other personnel of the retail environment for interacting with users or consumers on site. In such embodiments, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a user-specific electronic recommendation, as described herein, on a display screen of the retail computing device. In addition, the one or more user computing devices 111c1-111c3 and/or 112c1-112c3 may implement or execute an operating system (OS) or mobile platform such as Apple's iOS and/or Google's Android operation system. Any of the one or more user computing devices 111c1-111c3 and/or 112c1-112c3 may comprise one or more processors and/or one or more memories for storing, implementing, or executing computing instructions or code, e.g., a mobile application or a home or personal assistant application, as described in various embodiments herein. As shown in FIG. 1, skin puffiness model 108 may also be stored locally on a memory of a user computing device (e.g., user computing device 111c1).

User computing devices 111c1-111c3 and/or 112c1-112c3 may comprise a wireless transceiver to receive and transmit wireless communications 121 and/or 122 to and from base stations 111b and/or 112b. Pixel based images 202a, and/or 202c may be transmitted via computer network 120 to imaging server(s) 102 for training of model(s) and/or imaging analysis as describe herein.

In addition, the one or more user computing devices 111c1-111c3 and/or 112c1-112c3 may include a digital camera and/or digital video camera for capturing or taking digital images and/or frames (e.g., which can be any one or more of images 202a, and/or 202c). Each digital image may comprise pixel data for training or implementing model(s), such as AI or machine learning models, as described herein. For example, a digital camera and/or digital video camera of, e.g., any of user computing devices 111c1-111c3 and/or 112c1-112c3, may be configured to take, capture, or otherwise generate digital images (e.g., pixel based images 202a, and/or 202c) and, at least in some embodiments, may store such images in a memory of a respective user computing devices.

Still further, each of the one or more user computer devices 111c1-111c3 and/or 112c1-112c3 may include a display screen for displaying graphics, images, text, product recommendations, data, pixels, features, and/or other such visualizations or information as described herein. In various embodiments, graphics, images, text, product recommendations, data, pixels, features, and/or other such visualizations or information may be received by imaging server(s) 102 for display on the display screen of any one or more of user computer devices 111c1-111c3 and/or 112c1-112c3. Additionally, or alternatively, a user computer device may comprise, implement, have access to, render, or otherwise expose, at least in part, an interface or a guided user interface (GUI) for displaying text and/or images on its display screen.

Figure 2C:
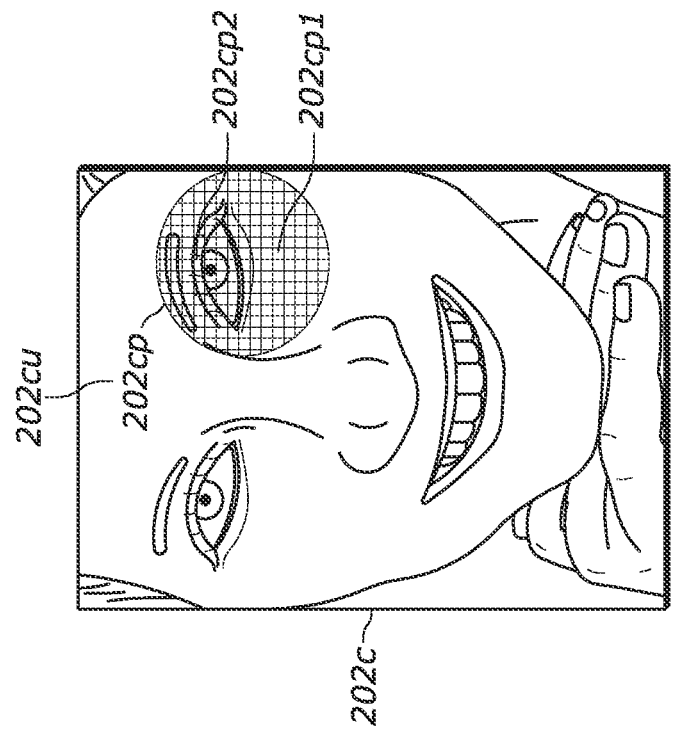
FIG. 2C illustrates a further example image and its related pixel data that may be used for training and/or implementing a skin puffiness model, in accordance with various embodiments disclosed herein.
Figure 2A:
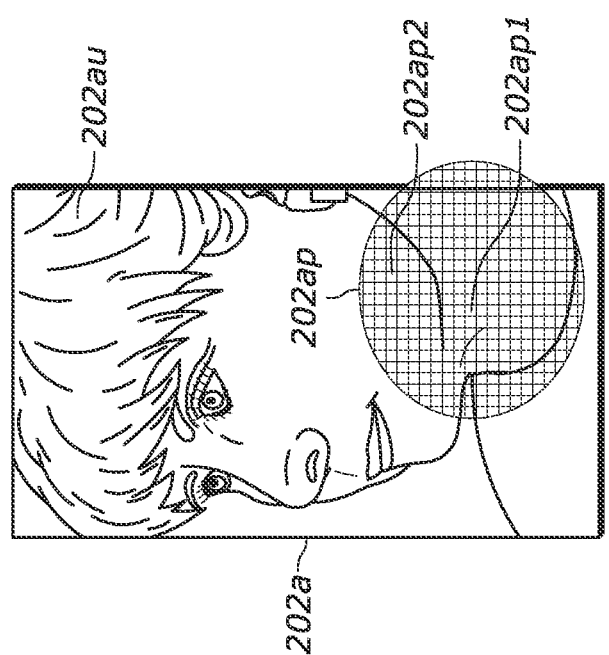
FIG. 2A illustrates an example image and its related pixel data that may be used for training and/or implementing a skin puffiness model, in accordance with various embodiments disclosed herein.

FIGS. 2A-2C illustrate example images 202a, and 202c that may be collected or aggregated at imaging server(s) 102 and may be analyzed by, and/or used to train, a skin puffiness model (e.g., an AI model such as a machine learning imaging model as describe herein). Each of these images may comprise pixel data (e.g., RGB data) corresponding representing feature data and corresponding to each of the personal attributes of the respective users 202au, and 202cu, within the respective image. The pixel data may be captured by a digital camera of one of the user computing devices (e.g., one or more user computer devices 111c1-111c3 and/or 112c1-112c3).

Generally, as described herein, pixel data (e.g., pixel data 202ap, and/or 202cp) comprises individual points or squares of data within an image, where each point or square represents a single pixel (e.g., pixel 202ap1 and pixel 202ap2) within an image. Each pixel may be a specific location within an image. In addition, each pixel may have a specific color (or lack thereof). Pixel color may be determined by a color format and related channel data associated with a given pixel. For example, a popular color format includes the red-green-blue (RGB) format having red, green, and blue channels. That is, in the RGB format, data of a pixel is represented by three numerical RGB components (Red, Green, Blue), that may be referred to as a channel data, to manipulate the color of pixel's area within the image. In some implementations, the three RGB components may be represented as three 8-bit numbers for each pixel. Three 8-bit bytes (one byte for each of RGB) is used to generate 24 bit color. Each 8-bit RGB component can have 256 possible values, ranging from 0 to 255 (i.e., in the base 2 binary system, an 8 bit byte can contain one of 256 numeric values ranging from 0 to 255). This channel data (R, G, and B) can be assigned a value from 0 255 and be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values. So (Red=220, Green=220, Blue=220) is a light gray (near white), and (Red=40, Green=40, Blue=40) is a dark gray (near black).

In this way, the composite of three RGB values creates the final color for a given pixel. With a 24-bit RGB color image using 3 bytes there can be 256 shades of red, and 256 shades of green, and 256 shades of blue. This provides 256×256× 256, i.e., 16.7 million possible combinations or colors for 24 bit RGB color images. In this way, the pixel's RGB data value shows how much of each of Red, and Green, and Blue pixel is comprised of. The three colors and intensity levels are combined at that image pixel, i.e., at that pixel location on a display screen, to illuminate a display screen at that location with that color. In is to be understood, however, that other bit sizes, having fewer or more bits, e.g., 10-bits, may be used to result in fewer or more overall colors and ranges.

As a whole, the various pixels, positioned together in a grid pattern, form a digital image (e.g., pixel data 202ap, and/or 202cp). A single digital image can comprise thousands or millions of pixels. Images can be captured, generated, stored, and/or transmitted in a number of formats, such as JPEG, TIFF, PNG and GIF. These formats use pixels to store represent the image.

FIG. 2A illustrates an example image 202a and its related pixel data (e.g., pixel data 202ap) that may be used for training and/or implementing a skin puffiness model (e.g., skin puffiness model 108), in accordance with various embodiments disclosed herein. Example image 202a illustrates a user skin area of user 202au or individual at a body area location comprising the user's neck. Image 202a is comprised of pixel data, including pixel data 202ap. Pixel data 202ap includes a plurality of pixels including pixel 202ap1 and pixel 202ap2. Pixel 202ap2 is a pixel positioned in image 202a comprising a body area location of the user, including the user's chin or cheek. Pixel 202ap1 is a dark pixel (e.g., a pixel with low R, G, and B values) positioned in image 202a where user 202au has a displacement amount of skin from the body area location (e.g., chin or cheek, e.g., of pixel 202ap2) as identifiable within the portion of the user skin area of pixel data 202ap. Pixel data 202ap includes various remaining pixels including remaining portions of user 202au, including areas of the user having a displacement amount of skin from other body area location(s) (e.g., check, neck, head, etc.). Pixel data 202ap further includes pixels representing further features including the user's position, posture, body portions, and other features as shown in FIG. 2A.

FIG. 2C illustrates a further example image 202cu and its related pixel data (e.g., 202cp) that may be used for training and/or implementing a skin puffiness model (e.g., skin puffiness model 108), in accordance with various embodiments disclosed herein. Example image 202c illustrates a user skin area of user 202cu or individual at a body area location comprising the user's head or face, and, in particular, eye. Image 202c is comprised of pixel data, including pixel data 202cp. Pixel data 202cp includes a plurality of pixels including pixel 202cp1 and pixel 202cp2. Pixel 202cp2 is a pixel positioned in image 202c comprising a body area location of the user, including the user's head or face, and, in particular, eye. Pixel 202cp1 is a dark pixel (e.g., a pixel with low R, G, and B values) positioned in image 202c where user 202cu has a puffy amount of skin, or otherwise a displacement amount of skin from the body area location (e.g., head, face, or eye, e.g., of pixel 202cp2) identifiable within the portion of the user skin area of pixel data 202cp. Pixel data 202cp includes various remaining pixels including remaining portions of user 202cu, including areas of the user having a displacement amount of skin from other body area location(s) (e.g., check, neck, etc.). Pixel data 202cp further includes pixels representing further features including the user's position, posture, body portions, and other features as shown in FIG. 2C.

Figure 3:
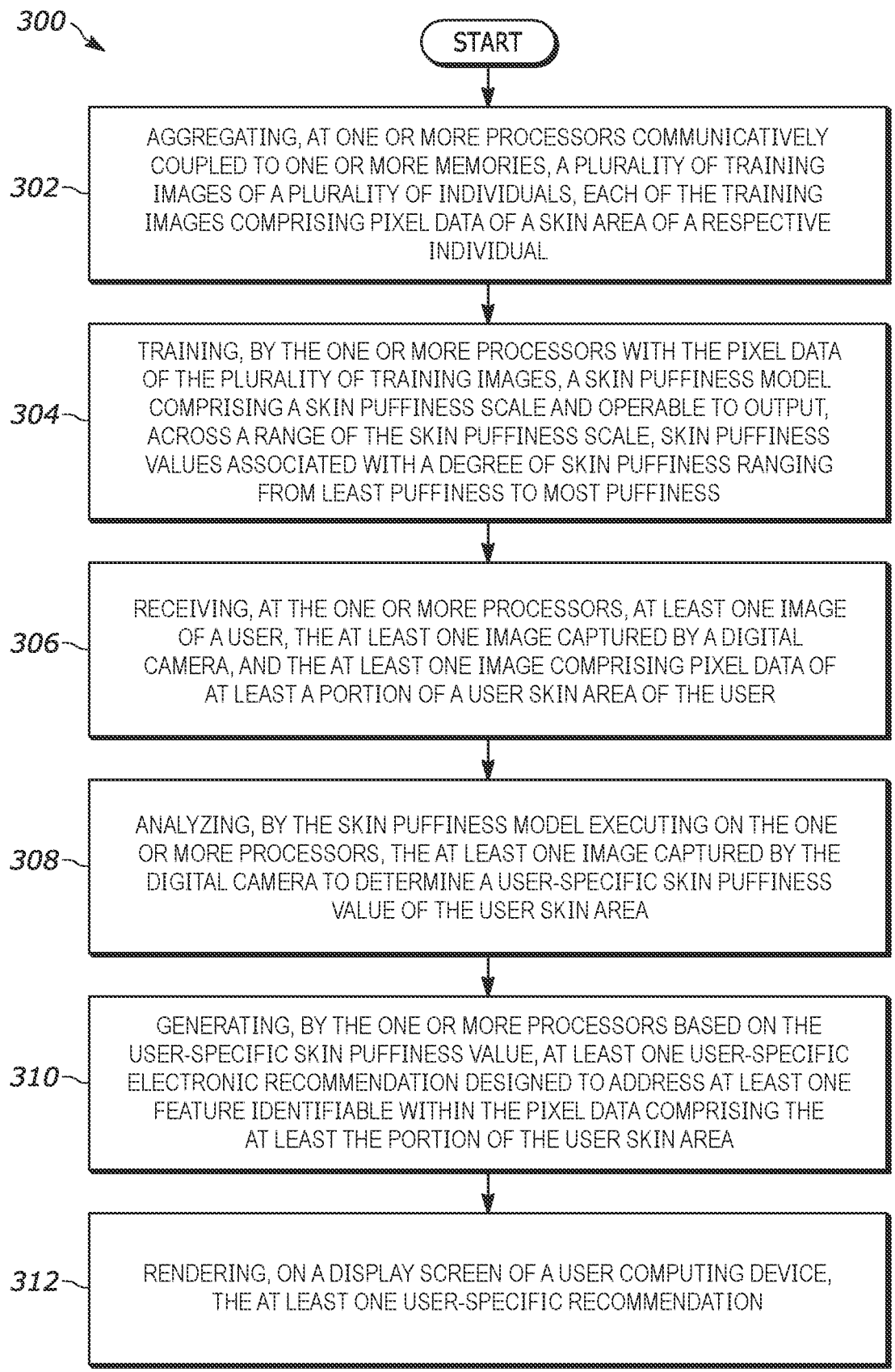
FIG. 3 illustrates a diagram of a digital imaging method of analyzing pixel data of an image of a skin area of a user for determining skin puffiness, in accordance with various embodiments disclosed herein.

FIG. 3 illustrates a diagram of a digital imaging method 300 of analyzing pixel data of an image (e.g., any of images 202a, and/or 202c) of a skin area of a user for determining skin puffiness, in accordance with various embodiments disclosed herein. Images, as described herein, are generally pixel images as captured by a digital camera (e.g., a digital camera of user computing device 111c1). In some embodiments an image may comprise or refer to a plurality of images such as a plurality of images (e.g., frames) as collected using a digital video camera. Frames comprise consecutive images defining motion, and can comprise a movie, a video, or the like.

At block 302, method 300 comprises aggregating, at one or more processors communicatively coupled to one or more memories, a plurality of training images of a plurality of individuals, each of the training images comprising pixel data of a skin area of a respective individual.

At block 304, method 300 comprises training, by the one or more processors with the pixel data of the plurality of training images, a skin puffiness model (e.g., skin puffiness model 108) comprising a skin puffiness scale and operable to output, across a range of the skin puffiness scale, skin puffiness values associated with a degree of skin puffiness ranging from least puffiness to most puffiness. In various embodiments, a skin puffiness scale can be an internalized scale or otherwise custom scale, unique to the skin puffiness model, where a least or small puffiness value may be determined from an image or set of images having skin areas with low skin puffiness values, i.e., images where the pixel data (e.g., lighter pixel data having higher RGB value(s)) indicates that a skin area is tight or stretched across a skin area of the user. Similarly, a most or large puffiness value may be determined from an image or set of images having skin areas with high skin puffiness values, i.e., images where the pixel data (e.g., darker pixel data having lower RGB value(s)) indicates that a skin area is tight in a skin area of the user. Additionally, or alternatively, skin puffiness model (e.g., skin puffiness model 108) is trained to detect patterns or groups of pixels within a given image. Such patterns or groups of pixels may be determined as having the same or similar RGB values (e.g., homogenous values) in similar areas or portions of the given image. For example, a pattern or group of pixels may have similar RGB values along one or more body area location(s), including, for example, a jawline, of a user having curves or contours. Such curves or contours, identifiable within the pixel data, may track along the underlying bone or muscle tissue of a user, which in an image of the user, are expressed as the patterns or groups of pixels having the same or similar RGB values (e.g., homogenous values) for a given portion of the image. In such instances, the patterns or groups of pixels can indicate a given body area location (e.g., a jawline), where a user-specific skin puffiness value may be determined based on the patterns or groups pixels. For example, in some embodiments, an amount of displacement of skin can be determined from a body area location (e.g., as determined from the patterns or groups of pixels). Additionally, or alternatively, a grouping or pattern of the pixels for the body area location itself can suggest taught or skin puffiness. For example, a tighter grouping or pattern of pixels may indicate taut skin, but a looser grouping or pattern may indicate loose skin.

In some embodiments, the skin puffiness scale may be a percentage scale, e.g., with skin puffiness model outputting skin puffiness values from 0% to 100%, where 0% represents least puffiness and 100% represents most puffiness. Values can range across this scale where a skin puffiness value of 67% represents one or more pixels of a skin area detected within an image that has a higher skin puffiness value than a skin puffiness value of 10% as detected for one or more pixels of a skin area within the same image or a different image (of the same or different user).

In some embodiments, the skin puffiness scale may be a numerical or decimal based scale, e.g., with skin puffiness model outputting skin puffiness values, e.g., from 0 to 10, where 0 represents least puffiness and 10 represents most puffiness. Values can range across this scale where a skin puffiness value of 78.9 represents one or more pixels of a skin area detected within an image that has a higher skin puffiness value than a skin puffiness value of 21.3 as detected for one or more pixels of a skin area within the same image or a different image (of the same or different user).

Skin puffiness values may be determined at the pixel level or for a given skin area (e.g., one or more pixels) in an image. Additionally, or alternatively, a comprehensive skin puffiness value, which can be a user-specific skin puffiness value as described herein, may be determined by averaging (or otherwise statistically analyzing) skin puffiness values for one or more pixels of a given skin area.

In various embodiments, skin puffiness model is an artificial intelligence (AI) based model trained with at least one AI algorithm. Training of skin puffiness model 108 involves image analysis of the training images to configure weights of skin puffiness model 108, and its underlying algorithm (e.g., machine learning or artificial intelligence algorithm) used to predict and/or classify future images. For example, in various embodiments herein, generation of skin puffiness model 108 involves training skin puffiness model 108 with the plurality of training images of a plurality of individuals, where each of the training images comprise pixel data of a skin area of a respective individual. In some embodiments, one or more processors of a server or a cloud-based computing platform (e.g., imaging server(s) 102) may receive the plurality of training images of the plurality of individuals via a computer network (e.g., computer network 120). In such embodiments, the server and/or the cloud-based computing platform may train the skin puffiness model with the pixel data of the plurality of training images.

In various embodiments, a machine learning imaging model, as described herein (e.g. skin puffiness model 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms may be included as a library or package executed on imaging server(s) 102. For example, libraries may include the TENSORFLOW based library, the PYTORCH library, and/or the SCIKIT-LEARN Python library.

Machine learning may involve identifying and recognizing patterns in existing data (such as training a model based on pixel data within images having pixel data of a skin area of a respective individual) in order to facilitate making predictions or identification for subsequent data (such as using the model on new pixel data of a new individual in order to determine a user-specific skin puffiness value of the user skin area of a user).

Machine learning model(s), such as the skin puffiness model described herein for some embodiments, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Image analysis may include training a machine learning based model (e.g., the skin puffiness model) on pixel data of images of one or more individuals comprising pixel data of respective skin areas of the one or more individuals. Additionally, or alternatively, image analysis may include using a machine learning imaging model, as previously trained, to determine, based on the pixel data (e.g., including their RGB values) one or more images of the individual(s), a user-specific skin puffiness value of the user skin area. The weights of the model may be trained via analysis of various RGB values of individual pixels of a given image. For example, dark or low RGB values (e.g., a pixel with values R=25, G=28, B=31) may indicate a displacement amount of skin from body area location(s) (e.g., check, neck, head, etc.) of a user. A red toned RGB value (e.g., a pixel with values R=215, G=90, B=85) may indicate irritated skin. A lighter RGB values (e.g., a pixel with R=181, G=170, and B=191) may indicate a lighter value, such as a normal skin tone color. Together, when a pixel with skin toned RGB value and/or a pixel with a lighter higher RGB value is positioned within a given image, or is otherwise surrounded by, a group or set of pixels having skin toned colors, then that may indicate an area on the skin where stretching of the skin occurs, respectively, as identified within the given image. In this way, pixel data (e.g., detailing one or more features of an individual, such as user skin area(s) of various individuals having different specific skin puffiness values(s) within 10,000 s training images may be used to train or use a machine learning imaging model to determine a user-specific skin puffiness value of a given user skin area.

In some embodiments training, by the one or more processors (e.g., of imaging server(s) 102) with the pixel data of the plurality of training images, the skin puffiness model (e.g., skin puffiness model 108) comprises training the skin puffiness model (e.g., skin puffiness model 108) to detect a displacement amount of skin from a body area location of the user to determine the user-specific skin puffiness value of the user skin area. In such embodiments the skin puffiness model may be trained to recognize that pixels with lighter values (e.g., lighter or higher RGB values) indicate a displacement amount of skin from body area location(s) (e.g., an arm) of a user. Skin puffiness model 108 may be trained to recognize (by assigning greater weighs to lighter pixels) that such lighter pixels against a pixel or group pixels having type skin tone colors indicates that displacement of skin from the body area location occurs. The amount of displacement can be determined from the amount or count of pixels detected from the lighter pixels to the body area location. For example, skin puffiness model 108 may be trained to recognize (by assigning greater weighs to pixels within a displacement zone between the lighter pixels and the body area location) that such displacement zone represents or is a displacement amount of skin from the body area location. In this way the skin puffiness model can identify patterns within the pixel data to determine a user-specific skin puffiness value of the user skin area.

Additionally, or alternatively, training, by the one or more processors (e.g., of imaging server(s) 102) with the pixel data of the plurality of training images, the skin puffiness model (e.g., skin puffiness model 108) may comprise training the skin puffiness model (e.g., skin puffiness model 108) to detect a folding amount of skin within the skin area to determine the user-specific skin puffiness value of the user skin area. In such embodiments the skin puffiness model may be trained to recognize that pixels with darker values (e.g., darker or lower RGB values) indicate a folding amount of skin within the skin area of a user. For example, pixel 202*ap*2 is a pixel positioned in image 202*a* comprising a body area location of the user, including the user's chin or cheek. Pixel 202*ap*1 is a dark pixel (e.g., a pixel with low R, G, and B values) positioned in image 202*a* where user 202*au* has a puffy amount of skin identifiable within the portion of the user skin area of pixel data 202*ap*. Skin puffiness model 108 may be trained to recognize (by assigning greater weighs to darker pixels) that such darker pixels (e.g., pixel 202*ap*1) against a pixel or group pixels having skin tone colors indicates that a puffy amount of skin occurs. The amount of puffiness can be determined from the amount or count of pixels detected from the dark pixels of the user skin area. For example, skin puffiness model 108 may be trained to recognize (by assigning greater weights to pixels within darker weights in a pattern across skin tone colors) that such pattern (e.g., of 202*ap*1) represents or is a swelling amount of skin from in the user skin area. In this way the skin puffiness model can identify patterns within the pixel data to determine a user-specific skin puffiness value of the user skin area.

In some embodiments, both a swelling amount of skin from in the user skin area and an amount of displacement of skin may be used to train skin puffiness model 108. For example, in such embodiments, training, by the one or more processors (e.g., imaging server(s) 102) with the pixel data of the plurality of training images, the skin puffiness model (e.g., skin puffiness model 108) may comprise training the skin puffiness model (e.g., skin puffiness model 108) to detect a displacement amount of skin from a body area location of the user in combination with a swelling amount of skin within the skin area (as described herein) to determine the user-specific skin puffiness value of the user skin area.

In various embodiments, a skin puffiness model (e.g., skin puffiness model 108) may be further trained, by one or more processors (e.g., imaging server(s) 102), with the pixel data of the plurality of training images, to output one or more location identifiers indicating one or more corresponding body area locations of respective individuals. In such embodiments, the skin puffiness model (e.g., skin puffiness model 108), executing on the one or more processors (e.g., imaging server(s) 102) and analyzing the at least one image of the user, can determine a location identifier indicating a body area location of the user's skin area. For example, body area locations may comprise a user's cheek, a user's neck, and a user's head. For example, each of images 202*a*, and 202*c* illustrate example body area locations including a user's neck, and a user's face, head, or eye, respectively.

With reference to FIG. 3, at block 306 method 300 comprises receiving, at the one or more processors (e.g., imaging server(s) 102 and/or a user computing device, such as user computing device 111*c*1), at least one image of a user. The at least one image may have been captured by a digital camera. In addition, the at least one image may comprise pixel data of at least a portion of a user skin area of the user.

At block 308, method 300 comprises analyzing, by the skin puffiness model (e.g., skin puffiness model 108) executing on the one or more processors (e.g., imaging server(s) 102 and/or a user computing device, such as user computing device 111*c*1), the at least one image captured by the digital camera to determine a user-specific skin puffiness value of the user skin area.

At block 310, method 300 comprises generating, by the one or more processors (e.g., imaging server(s) 102 and/or a user computing device, such as user computing device 111*c*1) based on the user-specific skin puffiness value, at least one user-specific electronic recommendation designed to address at least one feature identifiable within the pixel data comprising the at least the portion of the user skin area.

At block 312, method 300 comprises rendering, on a display screen of a user computing device, the at least one user-specific recommendation. A user computing device may comprise at least one of a mobile device, a tablet, a handheld device, or a desktop device, for example, as described herein for FIG. 1. In some embodiments, the user computing device (e.g., user computing device 111*c*1) may receive the at least one image comprising the pixel data of the at least the portion of the user skin area. In such embodiments, the user computing device may execute the skin puffiness model (e.g., skin puffiness model 108) locally and generate, based on output of the skin puffiness model (e.g., skin puffiness model 108), the user-specific recommendation. The user computing device 111*c*1 may then render the user-specific recommendation on its display screen.

Additionally, or alternatively, in other embodiments, the imaging server(s) 102 may analyze the user image remote from the user computing device to determine the user-specific skin puffiness value and/or user-specific electronic recommendation designed to address at least one feature identifiable within the pixel data comprising the at least the portion of the user skin area. For example, in such embodiments imaging server or a cloud-based computing platform (e.g., imaging server(s) 102) receives, across computer network 120, the at least one image comprising the pixel data of at the at least the portion of the user skin area. The server or a cloud-based computing platform may then execute skin puffiness model (e.g., skin puffiness model 108) and generate, based on output of the skin puffiness model (e.g., skin puffiness model 108), the user-specific recommendation. The server or a cloud-based computing platform may then transmit, via the computer network (e.g., computer network 120), the user-specific recommendation to the user computing device for rendering on the display screen of the user computing device.

In some embodiments, the user may submit a new image to the skin puffiness model for analysis as described herein. In such embodiments, one or more processors (e.g., imaging server(s) 102 and/or a user computing device, such as user computing device 111*c*1) may receive a new image of the user. The new image may be captured by a digital camera of user computing device 111*c*1. The new image may comprise pixel data of at least a portion of a user skin area of the user. The skin puffiness model (e.g., skin puffiness model 108) may then analyze, on the one or more processors (e.g., imaging server(s) 102 and/or a user computing device, such as user computing device 111*c*1), the new image captured by the digital camera to determine a new user-specific skin puffiness value of the user skin area. A new user-specific electronic recommendation or comment may be generated, based on the new user-specific skin puffiness value, regarding at least one feature identifiable within the pixel data of the new image. The new user-specific recommendation or comment (e.g., message) may then be rendered on a display screen of a user computing device of the user.

In some embodiments, a user-specific electronic recommendation may be displayed on the display screen of a user computing device (e.g., user computing device 111*c*1) with a graphical representation of the user's skin as annotated with one or more graphics or textual renderings corresponding to the user-specific skin puffiness value. In still further embodiments, the at least one user-specific electronic recommendation may be rendered in real-time or near-real time during or after receiving the at least one image having the user skin area.

In additional embodiments, a user-specific electronic recommendation may comprise a product recommendation for a manufactured product. In such embodiments, the user-specific electronic recommendation may be displayed on the display screen of a user computing device (e.g., user computing device 111*c*1) with instructions (e.g., a message) for treating, with the manufactured product, the at least one feature identifiable in the pixel data comprising the at least the portion of the user skin area. In still further embodiments, either the user computing device 111c1 and/or imaging server(s) may initiate, based on the product recommendation, the manufactured product for shipment to the user.

With regard to manufactured product recommendations, in some embodiments, one or more processors (e.g., imaging server(s) 102 and/or a user computing device, such as user computing device 111c1) may generate a modified image based on the at least one image of the user, e.g., as originally received. In such embodiments, the modified image may depict a rendering of how the user's skin is predicted to appear after treating the at least one feature with the manufactured product. For example, the modified image may be modified by updating, smoothing, or changing colors of the pixels of the image to represent a possible or predicted change after treatment of the at least one feature within the pixel data with the manufactured product. The modified image may then be rendered on the display screen of the user computing device (e.g., user computing device 111c1).

Additionally, or alternatively, a recommendation may be also made for the user's skin in the at least one image of the user, e.g., as originally received. In such embodiments, a user-specific electronic recommendation may display on the display screen of the user computing device (e.g., user computing device 111c1) with instructions for treating the at least one feature identifiable in the pixel data comprising the at least the portion of the user skin area.

Figure 4:
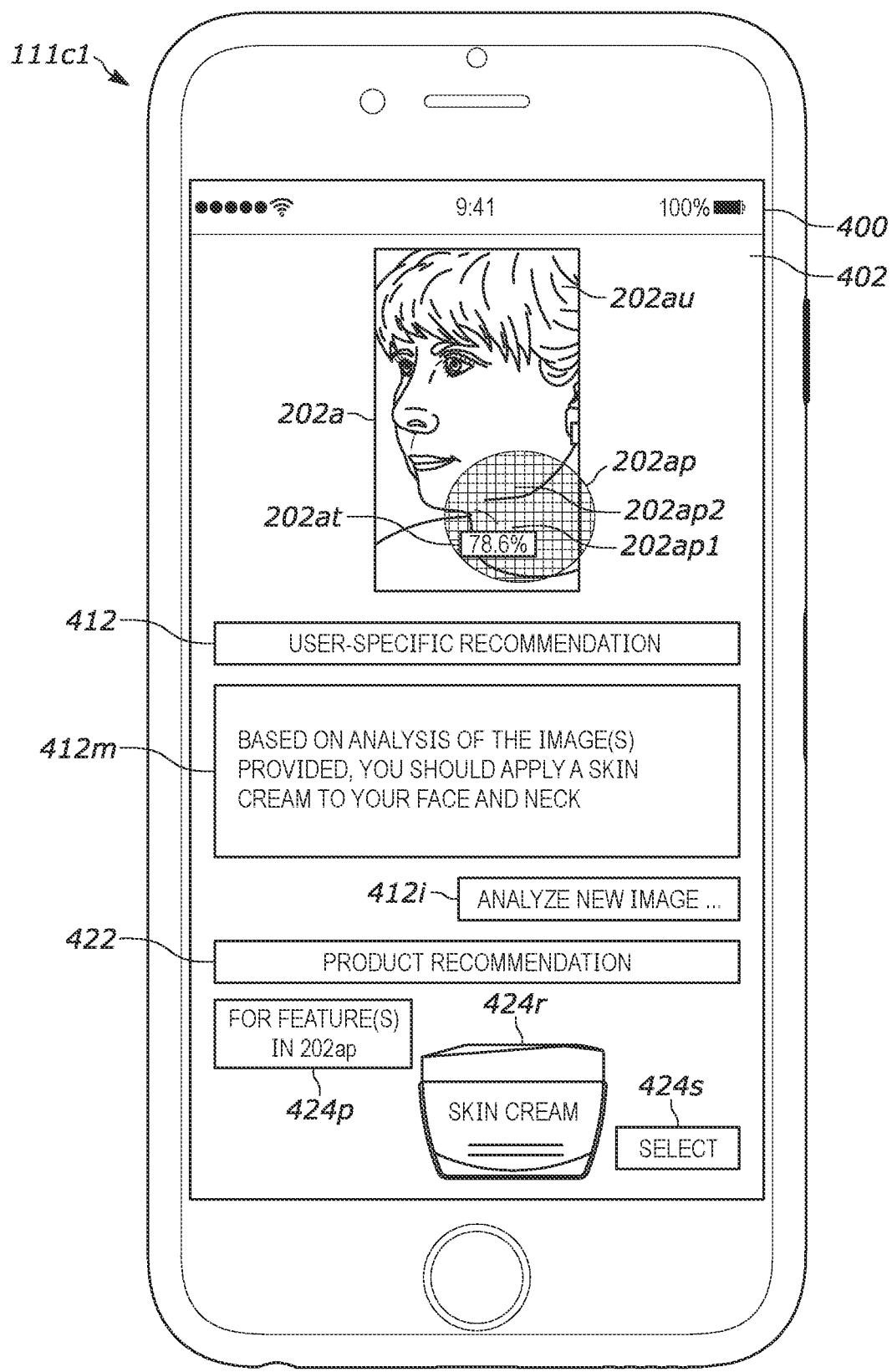
FIG. 4 illustrates an example user interface as rendered on a display screen of a user computing device in accordance with various embodiments disclosed herein.

FIG. 4 illustrates an example user interface 402 as rendered on a display screen 400 of a user computing device 111c1 in accordance with various embodiments disclosed herein. For example, as shown in the example of FIG. 4, user interface 402 may be implemented or rendered via an application (app) executing on user computing device 111c1.

For example, as shown in the example of FIG. 4, user interface 402 may be implemented or rendered via a native app executing on user computing device 111c1. In the example of FIG. 4, user computing device 111c1 is a user computer device as described for FIG. 1, e.g., where 111c1 is illustrated as an APPLE iPhone that implements the APPLE iOS operating system and has display screen 400. User computing device 111c1 may execute one or more native applications (apps) on its operating system. Such native apps may be implemented or coded (e.g., as computing instructions) in a computing language (e.g., SWIFT) executable by the user computing device operating system (e.g., APPLE iOS) by the processor of user computing device 111c1.

Additionally, or alternatively, user interface 402 may be implemented or rendered via a web interface, such as via a web browser application, e.g., Safari and/or Google Chrome app(s), or other such web browser or the like.

As shown in the example of FIG. 4, user interface 402 comprises a graphical representation (e.g., image 202a) of the user's skin. Image 202a may be the at least one image of the user (or graphical representation thereof), having pixels depicting skin puffiness, and as analyzed by the skin puffiness model (e.g., skin puffiness model 108) as described herein. In the example of FIG. 4, graphical representation (e.g., image 202a) of the user's skin is annotated with one or more graphics (e.g., area of pixel data 202a1) or textual rendering (e.g., text 202at) corresponding to the user-specific skin puffiness value. For example, the area of pixel data 202ap may be annotated or overlaid on top of the image of the user (e.g., image 202a) to highlight the area or feature(s) identified within the pixel data (e.g., feature data and/or raw pixel data) by the skin puffiness model (e.g., skin puffiness model 108). In the example of FIG. 4, the area of pixel data 202ap and the feature(s) identified within include the user-specific skin puffiness of the user's skin area, and other features shown in area of pixel data 202ap. In various embodiments, the pixels identified as the specific features indicating skin puffiness (e.g., pixel 202ap1 as a dark pixel indicating a folding amount of skin) or a displacement amount of skin from a body area location (e.g., pixel 202ap2 positioned at a cheek of the user) may be highlighted or otherwise annotated when rendered.

Textual rendering (e.g., text 202at) shows a user-specific skin puffiness value (e.g., 78.6%) which illustrates that the user has a skin puffiness value of 78.6% in the region defined by pixel data 202ap. The 78.6% value indicates that the user has a high amount of skin puffiness in the user skin area. It is to be understood that other textual rendering types or values are contemplated herein, where textual rendering types or values may be rendered, for example, as measurements, numerical values, amounts of pixels detected as lax, or derivatives thereof, or the like. Additionally, or alternatively, color values may use and/or overlaid on a graphical representation shown on user interface 402 (e.g., image 202a) to indicate a high degree of skin puffiness, a low degree of skin puffiness, or skin puffiness values within normal ranges or values (e.g., 25% to 50% skin puffiness value).

User interface 402 may also include or render a user-specific electronic recommendation 412. In the embodiment of FIG. 4, user-specific electronic recommendation 412 comprises a message 412m to the user designed to address at least one feature identifiable within the pixel data comprising the at least the portion of the user skin area. As shown in the example of FIG. 4, message 412m recommends to the user to apply a skin cream to the user's skin.

In particular, message 412m recommends use of a skin cream to the user's skin. The skin cream recommendation can be made based on the high skin puffiness value (e.g., 78.6%) as detected by the skin puffiness model where the skin cream product is designed to address the issue of skin puffiness detected in the pixel data of image 202a or otherwise assumed based on the high skin puffiness value. The product recommendation can be correlated to the identified feature within the pixel data, and the user computing device 111c1 and/or server(s) 102 can be instructed to output the product recommendation when the feature (e.g., excessive skin puffiness) is identified.

User interface 402 also include or render a section for a product recommendation 422 for a manufactured product 424r (e.g., skin cream as described above). The product recommendation 422 generally corresponds to the user-specific electronic recommendation 412, as described above. For example, in the example of FIG. 4, the user-specific electronic recommendation 412 is displayed on display screen 400 of user computing device 111c1 with instructions (e.g., message 412m) for treating, with the manufactured product (manufactured product 424r (e.g., skin cream)) at least one feature (e.g., 78.6% skin puffiness at pixel 202ap1) identifiable in the pixel data (e.g., pixel data 202ap) comprising the at least the portion of the user skin area (e.g., pixel 202ap1).

As shown in FIG. 4, user interface 402 recommends a product (e.g., manufactured product 424r (e.g., skin cream)) based on the user-specific electronic recommendation 412. In the example of FIG. 4, the output or analysis of image(s) (e.g., image 202a) of skin puffiness model (e.g., skin puffiness model 108), e.g., user-specific electronic recommendation 412 and/or its related values (e.g., 78.6% skin puffiness) or related pixel data (e.g., 202ap1 and/or 202ap2), may be used to generate or identify recommendations for corresponding product(s). Such recommendations may include products such as skin cream, cosmeceutical products, skin creams, and/or other such skin puffiness products, or the like, to address the user-specific issue as detected within the pixel data by the skin puffiness model (e.g., skin puffiness model 108).

In the example of FIG. 4, user interface 402 renders or provides a recommended product (e.g., manufactured product 424r) as determined by skin puffiness model (e.g., skin puffiness model 108) and its related image analysis of image 202a and its pixel data and various features. In the example of FIG. 4, this is indicated and annotated (424p) on user interface 402.

User interface 402 may further include a selectable UI button 424s to allow the user (e.g., the user of image 202a) to select for purchase or shipment the corresponding product (e.g., manufactured product 424r). In some embodiments, selection of selectable UI button 424s a may cause the recommended product(s) to be shipped to the user (e.g., individual 501) and/or may notify a third party that the individual is interested in the product(s). For example, either user computing device 111c1 and/or imaging server(s) 102 may initiate, based on user-specific electronic recommendation 412, the manufactured product 424r (e.g., skin cream) for shipment to the user. In such embodiments, the product may be packaged and shipped to the user.

In various embodiments, graphical representation (e.g., image 202a), with graphical annotations (e.g., area of pixel data 202ap), textual annotations (e.g., text 202at), user-specific electronic recommendation 412 may be transmitted, via the computer network (e.g., from an imaging server 102 and/or one or more processors) to user computing device 111c1, for rendering on display screen 400. In other embodiments, no transmission to the imaging server of the user's specific image occurs, where the user-specific recommendation (and/or product specific recommendation) may instead be generated locally, by the skin puffiness model (e.g., skin puffiness model 108) executing and/or implemented on the user's mobile device (e.g., user computing device 111c1) and rendered, by a processor of the mobile device, on display screen 400 of the mobile device (e.g., user computing device 111c1).

In some embodiments, any one or more of graphical representations (e.g., image 202a), with graphical annotations (e.g., area of pixel data 202ap), textual annotations (e.g., text 202at), user-specific electronic recommendation 412, and/or product recommendation 422 may be rendered (e.g., rendered locally on display screen 400) in real-time or near-real time during or after receiving the at least one image having the user skin area. In embodiments where the image is analyzed by imaging server(s) 102, the image may be transmitted and analyzed in real-time or near real-time by imaging server(s) 102.

In some embodiments, the user may provide a new image that may be transmitted to imaging server(s) 102 for updating, retraining, or reanalyzing by skin puffiness model 108. In other embodiments, a new image that may be locally received on computing device 111c1 and analyzed, by skin puffiness model 108, on the computing device 111c1.

In addition, as shown in the example of FIG. 4, the user may select selectable button 412i to for reanalyzing (e.g., either locally at computing device 111c1 or remotely at imaging server(s) 102) a new image. Selectable button 412i may cause user interface 402 to prompt the user to attach for analyzing a new image. Imaging server(s) 102 and/or a user computing device such as user computing device 111c1 may receive a new image of the user comprising pixel data of at least a portion of a user skin area of the user. The new image may be captured by the digital camera. The new image (e.g., just like image 202a) may comprise pixel data of at least a portion of the user skin area. The skin puffiness model (e.g., skin puffiness model 108), executing on the memory of the computing device (e.g., imaging server(s) 102), may analyze the new image captured by the digital camera to determine a new user-specific skin puffiness value of the user's skin area. The computing device (e.g., imaging server(s) 102) may generate, based on the new user-specific skin puffiness value, a new user-specific electronic recommendation or comment regarding at least one feature identifiable within the pixel data of the new image. For example, the new user-specific electronic recommendation may include a new graphical representation including graphics and/or text (e.g., showing a new user-specific skin puffiness value, e.g., 60%). The new user-specific electronic recommendation may include additional recommendations, e.g., that the user has incorrectly applied a skin cream as detected with the pixel data of the new image. A comment may include that the user has corrected the at least one feature identifiable within the pixel data (e.g., the user-specific skin puffiness value is now correct 25% 50%) by use of a recommended manufactured product or otherwise.

In some embodiments, a delta user-specific skin puffiness value may be generated, by the one or more processors (e.g., a processor of imaging server(s) 102 and/or user computing device such as user computing device 111c1) based on a comparison between the new user-specific skin puffiness value and the user-specific skin puffiness value. In such embodiments, the new user-specific recommendation or comment may be further based on the delta user-specific skin puffiness value. The delta user-specific skin puffiness value, a representation of the delta user-specific skin puffiness value (e.g., a graph or other graphical depiction), or a comment (e.g., text) based on the delta user-specific skin puffiness value, may be rendered on the display screen of the user computing device (e.g., user computing device 111c1) to illustrate or describe the difference (delta) between the new user-specific skin puffiness value and the user-specific skin puffiness value as previously determined. Additionally, or alternatively, a delta user-specific skin puffiness value may be generated based on a comparison between the new user-specific skin puffiness value and the user-specific skin puffiness value where the new user-specific recommendation comprises a recommendation of a hair removal product or hair removal technique for the user corresponding to the delta user-specific skin puffiness value. As one example, the delta user-specific puffiness value, determined based on a first image captured at a first time and a second image captured at a second time, may indicate whether the user's skin would benefit (e.g., experience less skin irritation and/or achieve a closer shave) from either a wet shaving razor, a dry shaving razor, and/or an electronic shaving razor, or based on other such razor characteristics. In such embodiments, the new user-specific recommendation may display the recommendation for a shaving razor, specific to the user's skin puffiness value(s), on a display screen of the user computing screen. Additionally, or alternatively, as further examples, the user computing device, based on a delta user-specific skin puffiness value for the user, may recommend a range of one or more hair removal product(s) or hair removal technique(s), which may include shaving using a wet razor, shaving using a dry shaver, removing hair with epilators, waxes, and/or the like.

In various embodiments, the new user-specific recommendation or comment may be transmitted via the computer network, from server(s) 102, to the user computing device of the user for rendering on the display screen of the user computing device.

In other embodiments, no transmission to the imaging server of the user's new image occurs, where the new user-specific recommendation (and/or product specific recommendation) may instead be generated locally, by the skin puffiness model (e.g., skin puffiness model 108) executing and/or implemented on the user's mobile device (e.g., user computing device 111c1) and rendered, by a processor of the mobile device, on a display screen of the mobile device (e.g., user computing device 111c1).

Aspects of the Disclosure

The following aspects are provided as examples in accordance with the disclosure herein and are not intended to limit the scope of the disclosure.

1. A digital imaging method of analyzing pixel data of an image of a skin area of a user for determining skin puffiness, the digital imaging method comprising the steps of: (a) aggregating, at one or more processors communicatively coupled to one or more memories, a plurality of training images of a plurality of individuals, each of the training images comprising pixel data of a skin area of a respective individual; (b) training, by the one or more processors with the pixel data of the plurality of training images, a skin puffiness model comprising a skin puffiness scale and operable to output, across a range of the skin puffiness scale, skin puffiness values associated with a degree of skin puffiness ranging from least puffiness to most puffiness; (c) receiving, at the one or more processors, at least one image of a user, the at least one image captured by a digital camera, and the at least one image comprising pixel data of at least a portion of a user skin area of the user; (d) analyzing, by the skin puffiness model executing on the one or more processors, the at least one image captured by the digital camera to determine a user-specific skin puffiness value of the user skin area; (e) generating, by the one or more processors based on the user-specific skin puffiness value, at least one user-specific electronic recommendation designed to address at least one feature identifiable within the pixel data comprising the at least the portion of the user skin area; and (f) rendering, on a display screen of a user computing device, the at least one user-specific recommendation.

2. The digital imaging method of aspect 1, wherein the at least one user-specific electronic recommendation is displayed on the display screen of the user computing device with a graphical representation of the user's skin as annotated with one or more graphics or textual renderings corresponding to the user-specific skin puffiness value.

3. The digital imaging method of any one of aspects 1-2, wherein the at least one user-specific electronic recommendation is rendered in real-time or near-real time, during, or after receiving the at least one image having the user skin area.

4. The digital imaging method of any one of aspects 1-3, wherein the at least one user-specific electronic recommendation comprises a product recommendation for a manufactured product.

5. The digital imaging method of aspect 4, wherein the at least one user-specific electronic recommendation is displayed on the display screen of the user computing device with instructions for treating, with the manufactured product, the at least one feature identifiable in the pixel data comprising the at least the portion of the user skin area.

6. The digital imaging method of aspect 4, further comprising the steps of initiating, based on the product recommendation, the manufactured product for shipment to the user.

7. The digital imaging method of aspect 4, further comprising the steps of generating, by the one or more processors, a modified image based on the at least one image, the modified image depicting how the user's skin is predicted to appear after treating the at least one feature with the manufactured product; and rendering, on the display screen of the user computing device, the modified image.

8. The digital imaging method of any one of aspects 1-7, wherein the at least one user-specific electronic recommendation is displayed on the display screen of the user computing device with instructions for treating the at least one feature identifiable in the pixel data comprising the at least the portion of the user skin area.

9. The digital imaging method of any one of aspects 1-8, wherein the skin puffiness model is an artificial intelligence (AI) based model trained with at least one AI algorithm.

10. The digital imaging method of any one of aspects 1-9, wherein the skin puffiness model is further trained, by the one or more processors with the pixel data of the plurality of training images, to output one or more location identifiers indicating one or more corresponding body area locations of respective individuals, and wherein the skin puffiness model, executing on the one or more processors and analyzing the at least one image of the user, determines a location identifier indicating a body area location of the user skin area.

11. The digital method of aspect 10, wherein the body area location comprises the user's head, the user's face, the user's cheek, the user's neck.

12. The digital method of any one of aspects 1-11, wherein training, by the one or more processors with the pixel data of the plurality of training images, the skin puffiness model comprises training the skin puffiness model to detect a displacement amount of skin from a body area location of the user to determine the user-specific skin puffiness value of the user skin area.

13. The digital method of any one of aspects 1-12, wherein training, by the one or more processors with the pixel data of the plurality of training images, the skin puffiness model comprises training the skin puffiness model to detect a folding amount of skin within the skin area to determine the user-specific skin puffiness value of the user skin area.

14. The digital method of any one of aspects 1-13, wherein training, wherein training, by the one or more processors with the pixel data of the plurality of training images, the skin puffiness model comprises training the skin puffiness model to detect a displacement amount of skin from a body area location of the user in combination with a folding amount of skin within the skin area to determine the user-specific skin puffiness value of the user skin area.

15. The digital method of any one of aspects 1-14, further comprising: receiving, at the one or more processors, a new image of the user, the new image captured by the digital camera, and the new image comprising pixel data of at least a portion of a user skin area of the user; analyzing, by the skin puffiness model executing on the one or more processors, the new image captured by the digital camera to determine a new user-specific skin puffiness value of the user skin area; generating, based on the new user-specific skin puffiness value, a new user-specific electronic recommendation or comment regarding at least one feature identifiable within the pixel data of the new image; and rendering, on a display screen of a user computing device of the user, the new user-specific recommendation or comment.

16. The digital imaging method of aspect 15, wherein a delta user-specific skin puffiness value is generated based on a comparison between the new user-specific skin puffiness value and the user-specific skin puffiness value, wherein the new user-specific recommendation or comment is further based on the delta user-specific skin puffiness value, and wherein the delta user-specific skin puffiness value, a representation of the delta user-specific skin puffiness value, or a comment based on the delta user-specific skin puffiness value, is rendered on the display screen of the user computing device.

17. The digital imaging method of aspect 15, wherein a delta user-specific skin puffiness value is generated based on a comparison between the new user-specific skin puffiness value and the user-specific skin puffiness value, wherein the new user-specific recommendation comprises a recommendation of a hair removal product or hair removal technique for the user corresponding to the delta user-specific skin puffiness value.

18. The digital method of any one of aspects 1-17, wherein the one or more processors comprises at least one of a server or a cloud-based computing platform, and the server or the cloud-based computing platform receives the plurality of training images of the plurality of individuals via a computer network, and wherein the server or the cloud-based computing platform trains the skin puffiness model with the pixel data of the plurality of training images.

19. The digital method of aspect 18, wherein the server or a cloud-based computing platform receives the at least one image comprising the pixel data of the at least the portion of the user skin area of the user, and wherein the server or a cloud-based computing platform executes the skin puffiness model and generates, based on output of the skin puffiness model, the user-specific recommendation and transmits, via the computer network, the user-specific recommendation to the user computing device for rendering on the display screen of the user computing device.

20. The digital method of any one of aspects 1-19, wherein the user computing device comprises at least one of a mobile device, a tablet, a handheld device, a desktop device, a home assistant device, or a personal assistant device.

21. The digital method of any one of aspects 1-20, wherein the user computing device receives the at least one image comprising the pixel data of at least the portion of the user skin area of the user, and wherein the user computing device executes the skin puffiness model and generates, based on output of the skin puffiness model, the user-specific recommendation, and renders the user-specific recommendation on the display screen of the user computing device.

22. The digital method of any one of aspects 1-22, wherein the at least one image comprises a plurality of images.

23. The digital method of aspect 22, wherein the plurality of images are collected using a digital video camera.

24. A digital imaging system configured to analyze pixel data of an image of a skin area of a user for determining skin puffiness, the digital imaging system comprising: an imaging server comprising a server processor and a server memory; an imaging application (app) configured to execute on a user computing device comprising a device processor and a device memory, the imaging app communicatively coupled to the imaging server; and a skin puffiness model trained with pixel data of a plurality of training images of individuals and operable to output, across a range of a skin puffiness scale, skin puffiness values associated with a degree of skin puffiness ranging from least puffiness to most puffiness, wherein the skin puffiness model is configured to execute on the server processor or the device processor to cause the server processor or the device processor to: receive, at the one or more processors, at least one image of a user, the at least one image captured by a digital camera, and the at least one image comprising pixel data of at least a portion of a user skin area of the user; analyze, by the skin puffiness model executing on the one or more processors, the at least one image captured by the digital camera to determine a user-specific skin puffiness value of the user skin area; generate, by the one or more processors based on the user-specific skin puffiness value, at least one user-specific electronic recommendation designed to address at least one feature identifiable within the pixel data comprising the at least the portion of the user skin area; and render, on a display screen of a user computing device, the at least one user-specific recommendation.

25. A tangible, non-transitory computer-readable medium storing instructions for analyzing pixel data of an image of a skin area of a user for determining skin puffiness, that when executed by one or more processors cause the one or more processors to: (a) aggregate, at one or more processors communicatively coupled to one or more memories, a plurality of training images of a plurality of individuals, each of the training images comprising pixel data of a skin area of a respective individual; (b) train, by the one or more processors with the pixel data of the plurality of training images, a skin puffiness model comprising a skin puffiness scale and operable to output, across a range of the skin puffiness scale, skin puffiness values associated with a degree of skin puffiness ranging from least puffiness to most puffiness; (c) receive, at the one or more processors, at least one image of a user, the at least one image captured by a digital camera, and the at least one image comprising pixel data of at least a portion of a user skin area of the user; (d) analyze, by the skin puffiness model executing on the one or more processors, the at least one image captured by the digital camera to determine a user-specific skin puffiness value of the user skin area; (e) generate, by the one or more processors based on the user-specific skin puffiness value, at least one user-specific electronic recommendation designed to address at least one feature identifiable within the pixel data comprising the at least the portion of the user skin area; and (f) render, on a display screen of a user computing device, the at least one user-specific recommendation.

ADDITIONAL CONSIDERATIONS

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital imaging method of analyzing pixel data of an image of a skin area of a user for determining skin puffiness, the digital imaging method comprising the steps of:
  a. aggregating, at one or more processors communicatively coupled to one or more memories, a plurality of training images of a plurality of individuals, each of the training images comprising pixel data of a skin area of a respective individual;
  b. training, by the one or more processors with the pixel data of the plurality of training images, a skin puffiness model comprising a skin puffiness scale and operable to output, across a range of the skin puffiness scale, skin puffiness values associated with a degree of skin puffiness ranging from least puffiness to most puffiness;
  c. receiving, at the one or more processors, at least one image of a user, the at least one image captured by a digital camera, and the at least one image comprising pixel data of at least a portion of a user skin area of the user;
  d. analyzing, by the skin puffiness model executing on the one or more processors, the at least one image captured by the digital camera to determine a user-specific skin puffiness value of the user skin area;
  e. generating, by the one or more processors based on the user-specific skin puffiness value, at least one user-specific electronic recommendation designed to address at least one feature identifiable within the pixel data comprising the at least the portion of the user skin area;

f. rendering, on a display screen of a user computing device, the at least one user-specific recommendation;

g. receiving, at the one or more processors, a new image of the user, the new image captured by the digital camera, and the new image comprising pixel data of at least a portion of a user skin area of the user;

h. analyzing, by the skin puffiness model executing on the one or more processors, the new image captured by the digital camera to determine a new user-specific skin puffiness value of the user skin area;

i. generating, based on the new user-specific skin puffiness value, a new user-specific electronic recommendation or comment regarding at least one feature identifiable within the pixel data of the new image; and rendering, on a display screen of a user computing device of the user, the new user-specific recommendation or comment;

wherein a delta user-specific skin puffiness value is generated based on a comparison between the new user-specific skin puffiness value and the user-specific skin puffiness value, wherein the new user-specific recommendation or comment is further based on the delta user-specific skin puffiness value, and wherein the delta user-specific skin puffiness value, a representation of the delta user-specific skin puffiness value, or a comment based on the delta user-specific skin puffiness value, is rendered on the display screen of the user computing device.

2. The digital imaging method of claim 1, wherein the at least one user-specific electronic recommendation is displayed on the display screen of the user computing device with a graphical representation of the user's skin as annotated with one or more graphics or textual renderings corresponding to the user-specific skin puffiness value.

3. The digital imaging method of claim 1, wherein the at least one user-specific electronic recommendation is rendered in real-time or near-real time, during, or after receiving the at least one image having the user skin area.

4. The digital imaging method of claim 1, wherein the at least one user-specific electronic recommendation comprises a product recommendation for a manufactured product.

5. The digital imaging method of claim 4, wherein the at least one user-specific electronic recommendation is displayed on the display screen of the user computing device with instructions for treating, with the manufactured product, the at least one feature identifiable in the pixel data comprising the at least the portion of the user skin area.

6. The digital imaging method of claim 4, further comprising the steps of:

initiating, based on the product recommendation, the manufactured product for shipment to the user.

7. The digital imaging method of claim 4, further comprising the steps of:

generating, by the one or more processors, a modified image based on the at least one image, the modified image depicting how the user's skin is predicted to appear after treating the at least one feature with the manufactured product; and rendering, on the display screen of the user computing device, the modified image.

8. The digital imaging method of claim 1, wherein the at least one user-specific electronic recommendation is displayed on the display screen of the user computing device with instructions for treating the at least one feature identifiable in the pixel data comprising the at least the portion of the user skin area.

9. The digital imaging method of claim 1, wherein the skin puffiness model is an artificial intelligence (AI) based model trained with at least one AI algorithm.

10. The digital imaging method of claim 1, wherein the skin puffiness model is further trained, by the one or more processors with the pixel data of the plurality of training images, to output one or more location identifiers indicating one or more corresponding body area locations of respective individuals, and wherein the skin puffiness model, executing on the one or more processors and analyzing the at least one image of the user, determines a location identifier indicating a body area location of the user skin area.

11. The digital method of claim 10, wherein the body area location comprises the user's cheek, the user's neck, the user's head, and the user's face.

12. The digital method of claim 1, wherein training, by the one or more processors with the pixel data of the plurality of training images, the skin puffiness model comprises training the skin puffiness model to detect a displacement amount of skin from a body area location of the user to determine the user-specific skin puffiness value of the user skin area.

13. The digital method of claim 1, wherein training, by the one or more processors with the pixel data of the plurality of training images, the skin puffiness model comprises training the skin puffiness model to detect a folding amount of skin within the skin area to determine the user-specific skin puffiness value of the user skin area.

14. The digital method of claim 1, wherein training, by the one or more processors with the pixel data of the plurality of training images, the skin puffiness model comprises training the skin puffiness model to detect a displacement amount of skin from a body area location of the user in combination with a folding amount of skin within the skin area to determine the user-specific skin puffiness value of the user skin area.

15. The digital imaging method of claim 1, wherein a delta user-specific skin puffiness value is generated based on a comparison between the new user-specific skin puffiness value and the user-specific skin puffiness value, wherein the new user-specific recommendation comprises a recommendation of a hair removal product or hair removal technique for the user corresponding to the delta user-specific skin puffiness value.

16. The digital method of claim 1, wherein the user computing device receives the at least one image of the user-specific recommendation on the display screen of the user computing device.

* * * * *